(12) United States Patent  (10) Patent No.: US 7,667,837 B2
Iwano et al.                (45) Date of Patent:    Feb. 23, 2010

(54) CAPILLARY TUBE FLOW CELL

(75) Inventors: Takeshi Iwano, Iruma (JP); Tsuyoshi Yamada, Iruma (JP); Xiaojing Zhou, Iruma (JP)

(73) Assignee: GL Sciences Incorporated (JP)

( * ) Notice: Subject to any disclaimer, the term of this patent is extended or adjusted under 35 U.S.C. 154(b) by 206 days.

(21) Appl. No.: 10/556,623

(22) PCT Filed: May 12, 2004

(86) PCT No.: PCT/JP2004/006660

§ 371 (c)(1), (2), (4) Date: Nov. 10, 2005

(87) PCT Pub. No.: WO2004/102166

PCT Pub. Date: Nov. 25, 2004

(65) Prior Publication Data

US 2007/0041009 A1    Feb. 22, 2007

(30) Foreign Application Priority Data

May 13, 2003  (JP) .............................. 2003-135067

(51) Int. Cl.
G01N 21/01   (2006.01)
G01N 1/10    (2006.01)

(52) U.S. Cl. ...................................... 356/246; 356/244

(58) Field of Classification Search ........... 356/244–246
See application file for complete search history.

(56) References Cited

U.S. PATENT DOCUMENTS

| 4,867,559 | A | * | 9/1989 | Bach ........................... 356/73 |
| 5,184,192 | A |   | 2/1993 | Gilby et al. |
| 5,274,227 | A |   | 12/1993 | Moring |
| 6,281,975 | B1 | * | 8/2001 | Munk ......................... 356/440 |

FOREIGN PATENT DOCUMENTS

| EP | 793 098 A | 9/1997 |
| JP | 2001-194294 A | 7/2001 |
| JP | 2002-267597 A | 9/2002 |

* cited by examiner

*Primary Examiner*—Michael P Stafira
(74) *Attorney, Agent, or Firm*—Robert J. Diaz; Hahn Loeser + Parks LLP

(57) ABSTRACT

Provided is a capillary tube flow cell used in analyses at very low flow rates and, particularly, in liquid chromatographic analyses. To ensure that high detection sensitivity and low noise can be realized, a flow cell which houses a liquid sample and exposes the liquid sample to radiant light for analysis purposes comprises a capillary tube which has a bent portion for incident light, a bent portion for emergent light and a linear passage of appropriate length formed between the bent portions, a passage portion of the capillary tube being inserted into a slit and the slit being provided with a light pass preventing portion.

9 Claims, 15 Drawing Sheets

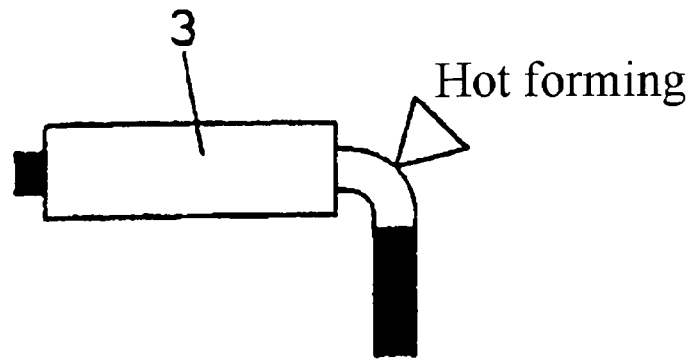
FIG. 4A
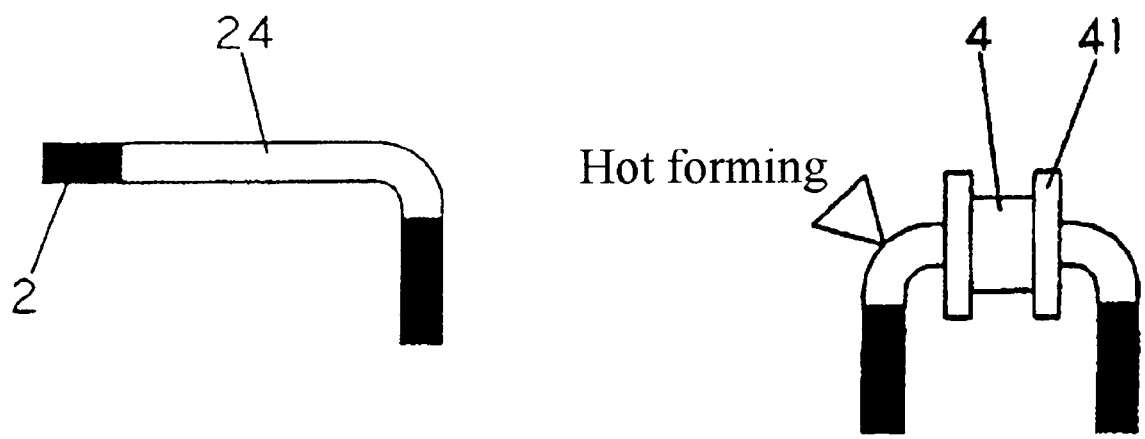
FIG. 4B  FIG. 4C

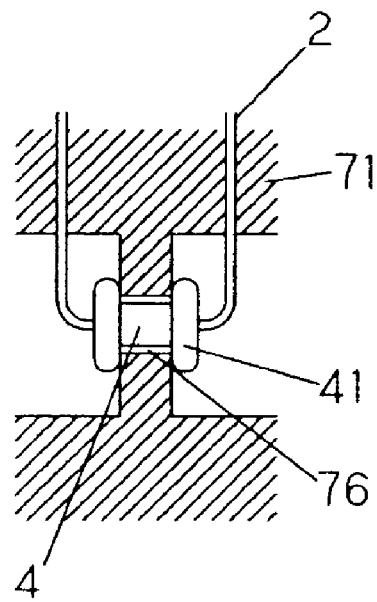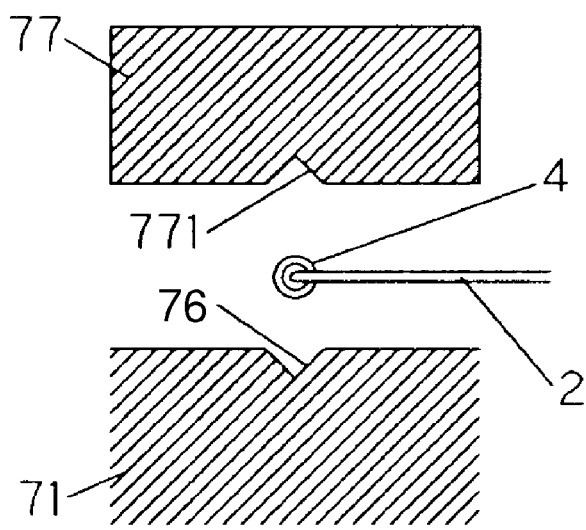
FIG. 9A  FIG. 9B
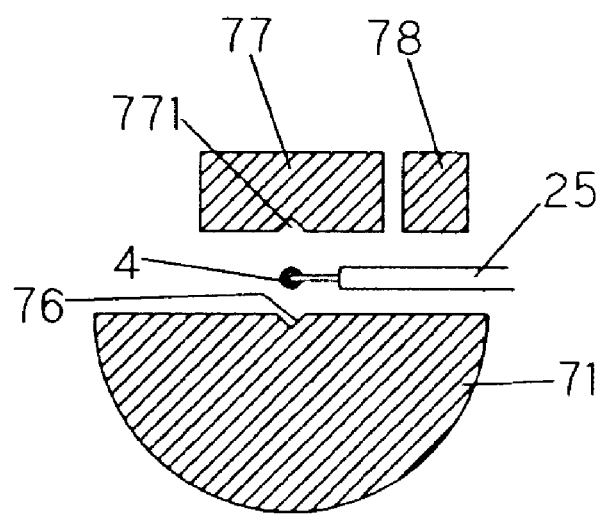
FIG. 9C

CAPILLARY TUBE FLOW CELL

TECHNICAL FIELD

The present invention relates to a capillary flow cell used in liquid chromatographic analyses and, in particular, in analyses at very low flow rates.

BACKGROUND OF THE ART

In analyses at very low flow rates, capillary tube flow cells have been frequently used because of their high detection sensitivity.

For example, capillary tube flow cells are often used when mass spectrometers are used as detectors for the capillary electrophoretic process and liquid chromatograph and, in particular, when the detection of absorbance, fluorescence, etc. is performed.

In a method described in the U.S. Pat. No. 5,057,216, a capillary tube is inserted into an optical passage, the capillary material is softened by heating both ends of the capillary tube, and the two ends are bent and formed in the shape of the letter Z or U, whereby a capillary flow cell is fabricated.

And for this bending, the Japanese Patent Laid-Open No. 2002-267597 describes a bending method which involves threading a capillary tube through a fine tube, supporting this fine tube in a sandwiched manner between top and bottom beds which are obtained by division into top and bottom portions, this apparatus being called a fine tube fixing holder, heating both ends of the fine tube, and causing the capillary tube outside the beds to droop down under its own weight, whereby bending is performed.

In a case where a flow cell in which a capillary tube is used is adopted and light is caused to become incident in the same direction as the direction of a flow passage of the capillary tube, it is possible to ensure an optical passage length of several millimeters, and this enables detection sensitivity to be improved.

In conventional methods of fabricating a flow cell in which a capillary tube is used, it is necessary to exfoliate a polyimide coating of a portion which transmits light by use of a gas burner and the like and after that, the capillary tube is bent and formed in the shape of the letter U or Z.

However, because of the minimization of flow rate these capillary tubes have become increasingly small and clogging has become apt to occur. At the same time, because of the diversification of samples, it is necessary to change the diameter of capillary tubes and hence the necessity of replacement of capillary tubes has increased. However, the replacement work is very difficult and requires specialized knowledge and experience and in addition, it takes time to replace capillary tubes. Therefore, general users cannot easily replace capillary tubes. In particular, it takes time to adjust an optical system of a capillary tube, thereby making analysis operations difficult.

Furthermore, in bending a capillary tube, it is necessary to provide a slit in the portion of a capillary tube from which a polyimide coating has been exfoliated, thereby to cut off light other than the light in the optical axis (stray light). However, if the slit diameter is too small on this occasion, detection noise increases because the quantity of transmitted light of the capillary is small.

Furthermore, when transmitted light is supplied and, in particular, when incoming light is weak, an increase in the noise of a detector becomes a serious problem in performance. In addition, because very low flow rates are handled in liquid chromatographic analyses in which a capillary tube is used, flow velocities become low. Therefore, it takes time to perform analyses if the piping is long, thereby bringing about changes due to temperature, quantity of light, etc. and there is a possibility that accurate detection may be impaired.

For this reason, simple replace means of capillary tubes is needed.

SUMMARY OF THE INVENTION

Therefore, in a flow cell in which a capillary tube is used, it is an object of the present invention to provide a capillary tube which any one can replace easily and in a short time without requiring any adjustment when it is necessary to replace the capillary tube.

Also, an object of the present invention is to ensure that by enabling a capillary flow cell to be spaced from the body of a detector, with the result that the capillary flow cell can be disposed near both the column and the LC/MS interface, that piping can be shortened, that the shortest connection among flow cell, column and LC/MS interface become possible, that it becomes possible to place the capillary flow cell in an oven, and that detection is stable even if varying temperature.

Also, an object of the present invention is to ensure that even when incident light is weak, high detection sensitivity and low noise can be realized and that incident light can be received by use of an optical fiber.

The capillary tube flow cell of the present invention is a capillary tube flow cell in which a liquid sample is delivered and exposed in a desired incident light for analysis purposes, characterized by comprising a capillary tube which has a bent portion for incident light and a bent portion for emergent light and in which a linear passage of appropriate length is formed between the bent portions, a passage portion of the capillary tube being inserted into a slit and the slit being provided with a light pass preventing portion.

Furthermore, the capillary tube flow cell of the present invention is characterized in that the light pass preventing portion is formed in ring shape and fitted into the slit or formed in the slit.

Furthermore, the capillary tube flow cell of the present invention is characterized in that a pipe having a diameter through which the capillary tube passes is used as the slit.

Furthermore, the capillary tube flow cell of the present invention is characterized in that the slit is formed so that the slit has a diameter which is 0.05 to 1 mm larger than the capillary tube.

Furthermore, the capillary tube flow cell of the present invention is characterized in that through holes are formed on both side surfaces of a cell body, that a lens holder which holds a ball lens is placed insertable and fixable in the through hole, that a wall is formed between the through holes, that a groove is formed in the wall that a capillary tube is installed by use of a pipe type slit which is inserted through the groove, and that the capillary tube is fixed by a tube holder.

Furthermore, the capillary tube flow cell of the present invention is characterized in that the groove is a triangular groove.

Furthermore, the capillary tube flow cell of the present invention is characterized in that the cell body is covered with a thermally insulating synthetic resin cover.

Also, the capillary tube flow cell of the present invention is characterized in that there is provided a capillary tube in which a cell body has a capillary tube which has a bent portion for incident light, a bent portion for emergent light and a passage between the bent portions in a cell body, that a capillary tube unit is constituted by positioning ball lenses in face-to-face relationship with the bent portion for incident light and the bent portion for emergent light each outside the bent portions, one of the ball lenses being removably provided with a light incidence unit having a light supply portion in communication with a light source and the other ball lens being removably provided with a sensor unit having a sensor.

Furthermore, the capillary tube flow cell of the present invention is characterized in that the removable light incidence unit is connected to the light source and the capillary tube unit by use of an optical fiber and that the capillary tube unit is connected to LC/MS.

According to the present invention described above, there is provided a capillary tube flow cell in which a liquid sample is delivered and exposed in a desired incident light for analysis purposes, which comprises a capillary tube which has a bent portion for incident light and a bent portion for emergent light and in which a linear passage of appropriate length is formed between the bent portions, a slit being inserted into a passage portion of the capillary tube and the slit being provided with a light pass preventing portion. Therefore, light introduced into the capillary tube can be focused on a lumen. For this reason, even in the case of weak light such as from an optical fiber, it is possible to avoid an increase in the noise of a detector which might be achieved with an increase in the quantity of light, so that high sensitivity and low noise can be realized even in the case of weak incident light. Furthermore, stray light can be cut off by the ring and the focusing of light is promoted. For this reason, it has become possible to use an optical fiber in spite of its weak incident light.

Furthermore, there is provided a capillary tube in which a cell body has a capillary tube which has a bent portion for incident light, a bent portion for emergent light and a passage between the bent portions in a cell body, that a capillary tube unit is constituted by positioning ball lenses in face-to-face relationship with the bent portion for incident light and the bent portion for emergent light each outside the bent portions, one of the ball lenses being removably provided with a light incidence unit having a light supply portion in communication with a light source and the other ball lens being removably provided with a sensor portion unit having a sensor. Therefore, because light can be introduced and incident on the capillary tube by use of an optical fiber, the capillary tube unit be can be spaced from the body of a detector. As a result of this, the shortest connection among flow cell, column and LC/MS interface becomes possible when the detector is used as a monitor of LC/MS. Also, it becomes possible to place the capillary flow cell into an oven, and detection performance which is stable even at varying temperature can be exhibited.

The greatest advantage of the present invention described above is that the capillary tube and the ball lens are integrated as the capillary tube unit, and that this capillary tube unit is formed so as to be connectable to and separable from the sensor portion unit and the light incidence unit, whereby the capillary tube unit can be replaced easily as a complete part without requiring any adjustment of the optical system.

For this reason, any one can easily prevent the clogging of the capillary tube and exchange with a desired flow cell according to flow rates.

BRIEF DESCRIPTION OF THE DRAWINGS

FIG. 4A is a diagram to explain the bending of a capillary tube;

FIG. 4B is a diagram to explain the bending of a capillary tube;

FIG. 4C is a diagram to explain the bending of a capillary tube;

FIG. 9A is an exploded enlarged view to explain this portion;

FIG. 9B is an exploded enlarged view to explain this portion;

FIG. 9C is an exploded enlarged view to explain this portion;

DETAILED DESCRIPTION OF THE DRAWINGS

Figure 1:
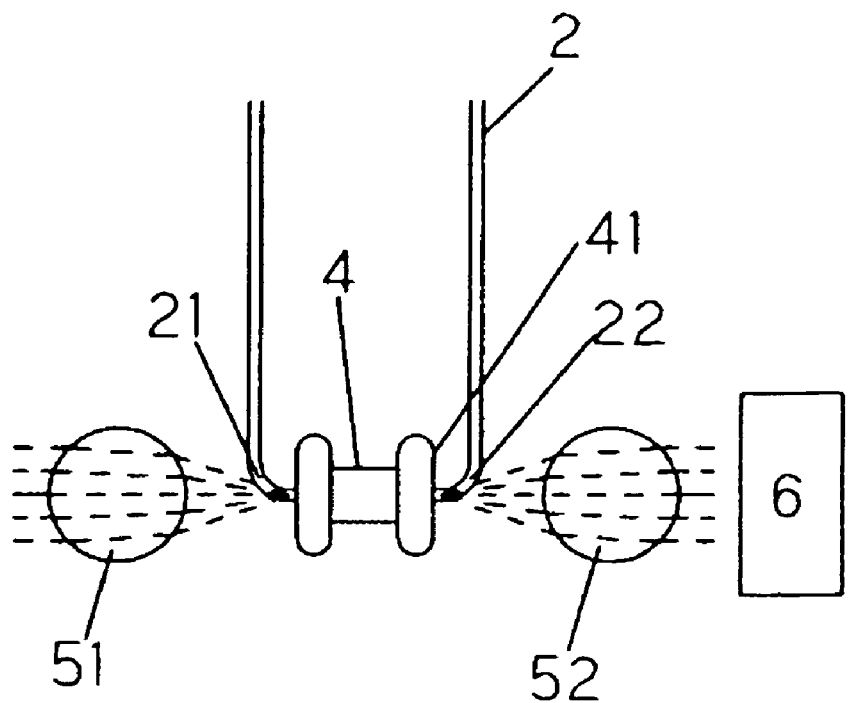
FIG. 1 is a schematic explanatory diagram of the present invention.

Hereinafter, the present invention will be described in detail by using examples shown in the drawings.

First, the basic configurations shown in FIGS. 1 to 5B are described.

The reference numeral 1 denotes a capillary flow cell and formed in the shape of the letter U or Z by bending and forming a capillary tube 2. The capillary tube 2 is a fused silica tube and is coated with a polyimide resin. A first bent portion is called a bent portion for incident light 21 and a second bent portion is called a bent portion for emergent light 22. A linear passage portion between the bent portion for incident light 21 and the second bent portion for emergent light 22 is called a lumen portion 23.

For the formation of the two bent portions, as shown in FIGS. 4A to 4C, a portion to be bent is inserted into a long pipe 3 and the capillary tube 2 at pipe 3 ends is heated and bent (FIG. 4A). The reason why the long pipe 3 is used in the working is that during the working of one side of the capillary tube 2, a flame for hot forming is prevented thereby from reaching the opposite side of the pipe 3 so that unintended portion is not changed in shape. During the hot forming, the polyimide coating of the capillary tube 2 is exfoliated.

Because in the portion of the capillary tube 2 covered with the long pipe 3, the polyimide coating cannot be exfoliated, the polyimide coating in this portion must be exfoliated (FIG. 4B). The length of the portion from which the polyimide coating is exfoliated is enough if it is longer than the optical path length, i.e., the lumen 23 plus 2 mm or so.

Next, the capillary tube 2 is inserted into the pipe 4 which is used as a slit. A desired length of the pipe 4 is a little shorter than the optical path length and 1 mm to 2.5 mm shorter than the optical path length.

If the pipe 4 has a high thermal conductivity, this is convenient for the forming of the capillary tube. Therefore, a metal pipe, for example, a stainless steel pipe is used.

The side of the capillary tube 2 which has not been bent is heated and bent (FIG. 4C).

Figure 5A:
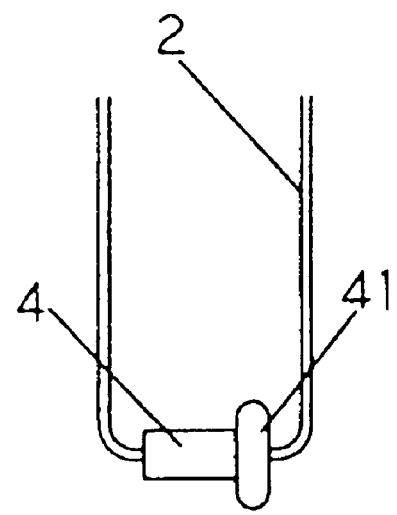
FIG. 5A is a partial explanatory view of a slit portion in an example of the present invention.
Figure 5B:
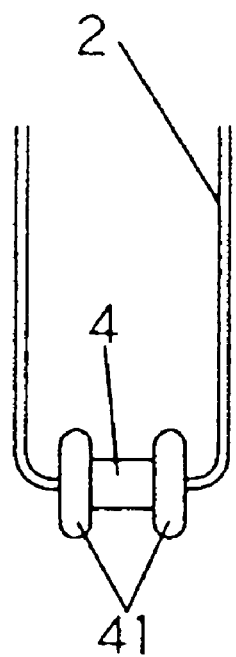
FIG. 5B is a partial explanatory view of a slit portion in an example of the present invention.

A ring 41 which has the same inner diameter as that of the pipe 4 or little smaller inner diameter than that of the pipe 4 and an outside diameter larger than a triangular groove, which will be described later, is attached to one side or both sides of the pipe 4. In this case, the same effect is obtained also from a flanged pipe (FIGS. 5A and 5B).

A desired inner diameter of the pipe 4 is 0.05 to 0.7 mm or so larger than the outside diameter of the capillary tube 2. Detection sensitivity increases with decreasing inner diameter of the pipe 4. However, noise also increases with decreasing inner diameter of the pipe 4. In this example, a pipe 4 having an inner diameter of 0.8 mm was used for an outside diameter of the capillary tube 2 of 0.375 mm.

When the slit is formed as a through hole as in the optical system of the cell portion, the ring 41 can be installed adjacent to the through hole.

The reference numerals 51, 52 denote a ball lens. The ball lens 51 and the ball lens 52 are installed in face-to-face relationship, respectively, with the bent portion for incident light 21 and the bent portion for emergent light 22, each on their installed sides. The ball lens 51 is installed in such a manner that the transmitted light is focused on a lumen portion 23, and the ball lens 52 is installed so that it efficiently sends rays of light which have passed the lumen portion 23 to a detection section 6.

It is preferred that the ball lens 51 be installed to ensure that light collides against the wall surface of the capillary tube 2 as little as possible and that parallel rays possibly pass the lumen portion 23.

Figure 3A:
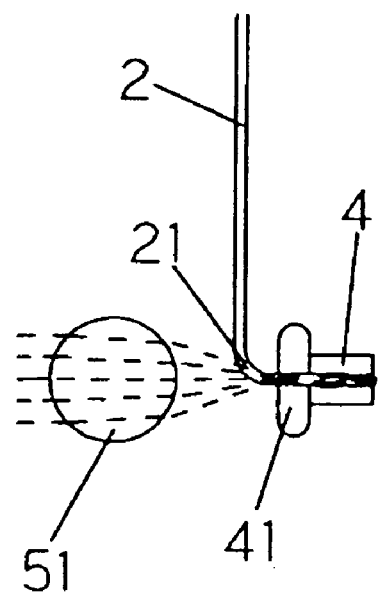
FIG. 3A is a diagram to explain the converging condition of incident light in the present invention.
Figure 3B:
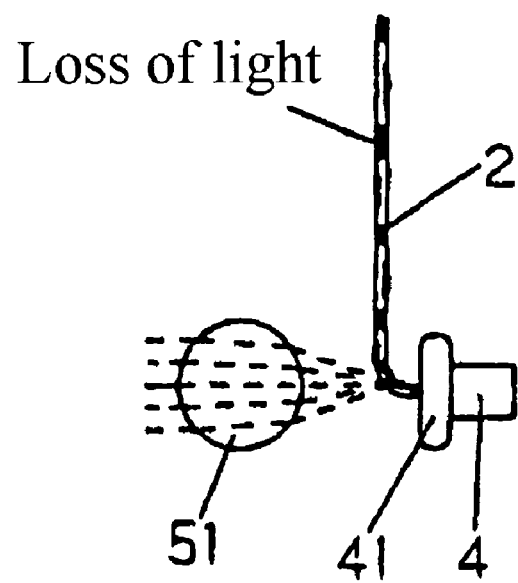
FIG. 3B is a diagram to explain a different converging condition of incident light in the present invention.

For this purpose, the ball lens 51 is installed in such a manner that the light which enters the ball lens is focused on the bent portion for incident light 21 of the capillary tube 2, in particular, immediately before the slit 4, i.e., at the entry (FIG. 3A).

In the capillary tube 2 bent in the form of the letter U or Z, a bending radius R occurs in the bent portion for incident light 21 and the bent portion for emergent light 22. If incident light is focused on this bent portion for incident light 21, the light radiates and dissipates in directions other than the direction of the lumen portion 23, resulting in a large loss of light. Therefore, it is necessary to prevent this. Also, because of the use of the ball lens 51, when incident light is introduced directly on the outer surface of the bent portion for incident light 21, it is necessary to prevent the light from being reflected and the quantity of light passing through the lumen portion 23 from decreasing.

A construction for this purpose was devised to install the ball lens 51 and to focus the light immediately before the slit 4.

EXAMPLES

Next, examples shown in FIGS. 6 to 11 will be described.

The reference numeral 7 denotes a capillary tube unit, which is an example of a concrete construction in which the capillary tube 2 and ball lenses 51, 52 shown in FIG. 1 are built. The capillary tube 2 is formed in the shape of the letter U in FIG. 6, and a capillary tube 2 formed in the shape of the letter Z is used in other figures. The capillary tube unit 7 is connected to a sensor system unit 8 on one side and to a light incidence unit 9 on the other side.

The capillary tube unit 7 will be described with reference to FIGS. 6 to 11.

The capillary tube 2 is formed in the shape of the letter U or Z, the slit 4 is inserted in the lumen portion 22, and the rings 41, 41 are formed on both ends.

The capillary tube unit 7 is constituted by a cell body 71 formed in the shape of a cylindrical column and a synthetic resin cover 72 which covers the outside of the cell body 71. It is preferred that synthetic resins having heat insulating properties, such as polyacetal, PEEK and polycarbonate, be used as this resin cover 72. It is convenient that this cover 72 is formed in the shape of a semi-doughnut of almost the same shape and supports the cell body 71 in a sandwiching manner thereby to fix the cell body.

Owing to this construction the capillary tube unit tolerates to change in ambient temperature and it is unnecessary to control the temperature of the capillary tube unit by placing it in an oven. In the cell body 71, a semicircular notched part 70 having an appropriate width is formed in the middle part. Through holes 74, 74 which house inserted lens holders 8, 8 are drilled from both sides to the center of the cylindrical column and a groove 76, in which the slit 4 is placed, is formed in a wall 75 between the two through holes 74, 74.

Figure 10:
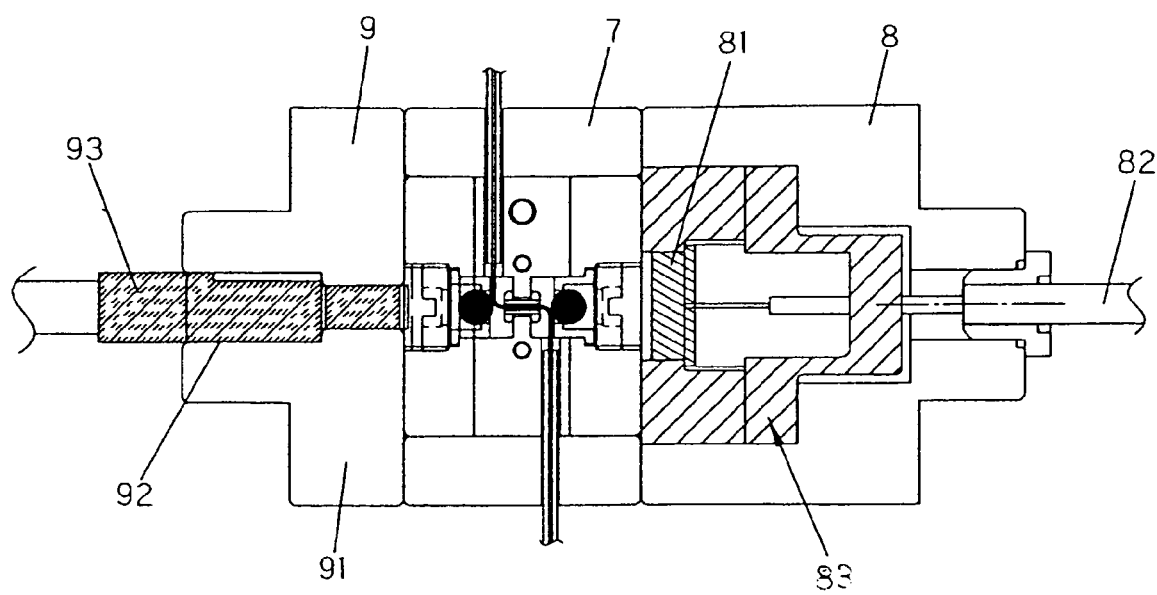
FIG. 10 is a partial longitudinal enlarged view to explain a unit portion in an example of the present invention.
Figure 11:
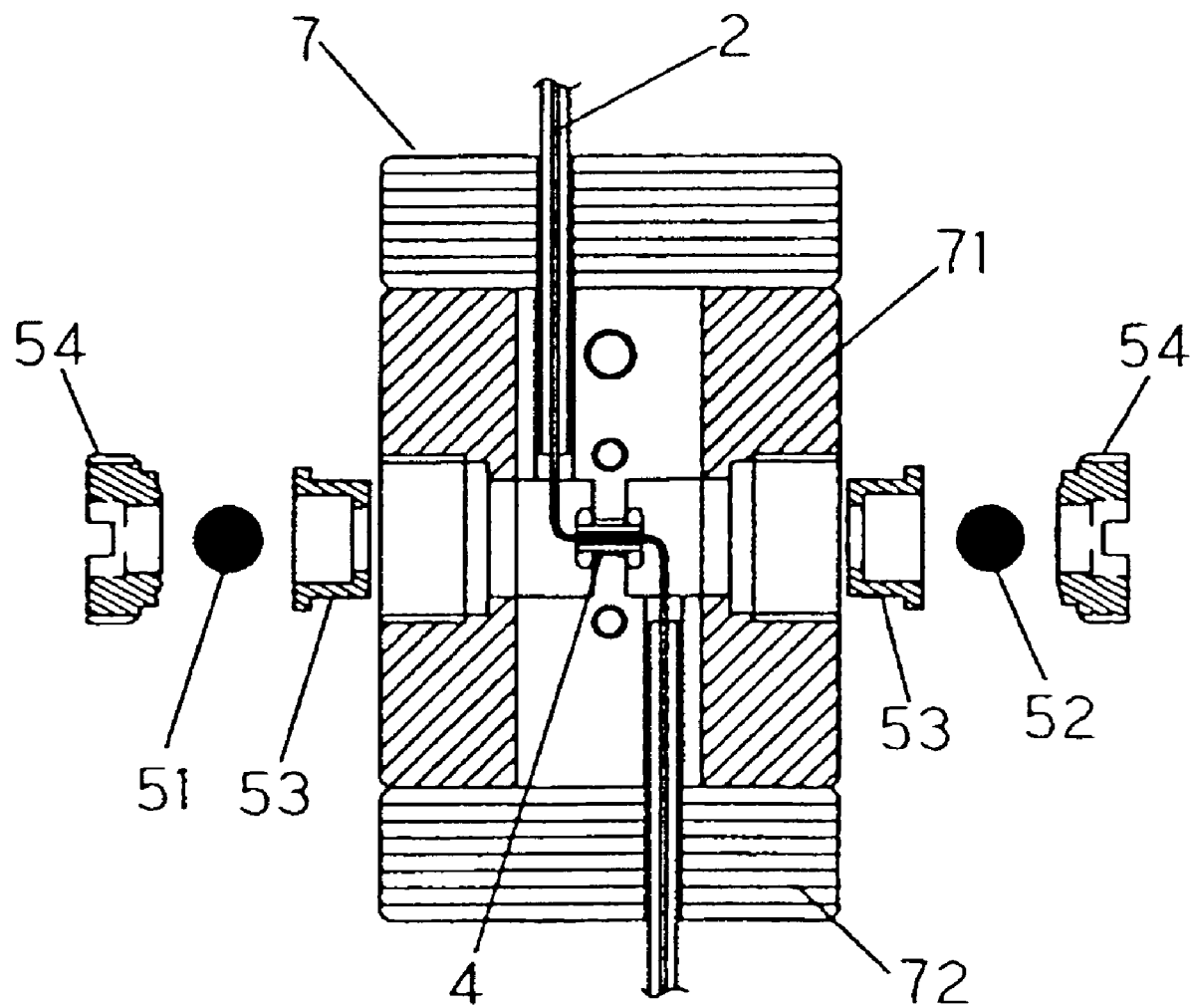
FIG. 11 is an exploded longitudinal enlarged view to explain a capillary tube unit portion in an example of the present invention.

Grooves 73, 73 in which the capillary tube 2 is placed when the slit 4 of the capillary tube 2 is placed in the groove 76 formed in a wall 75 are formed in a notched part 70 so as to provide communication with the wall 75 and the U-shaped capillary tube 2 is placed on the groove 76 and the grooves 73, 73. In installing the Z-shaped capillary tube 2, as shown in FIGS. 10 and 11, the grooves 73, 73 are formed symmetrically with respect to the groove 76.

Subsequently, the capillary tube 2 is fixed by use of holding plates 77, 78 which hold the slit 4 and screws etc. On that occasion, it is recommended that for the holding plate 77, the grove 76 be a triangular groove and that a triangular groove 771 be formed so as to match the grove 76. Also, it is recommended that the notched part 70 be covered with a plate body having the shape of a semicircle.

It is also possible that these holding plates 77, 78 or the semicircular plate body covering the notched part 70 is formed integrally with the portion forming the remaining part of the cell body 71.

The ball lens 51 or 52 is installed on a lens holder 53 and lens covers 54 are placed on the ball lens, whereby the ball lens 51 or 52 is fixed.

The groove 76 and a triangular groove 781 formed in the holding plate 78 hold the slit 4, identifies the position of the lumen portion 22 of the capillary tube 2 and cause the lumen portion 22 of the capillary tube to coincide with the optical axis. For this reason, the positions of the ball lens 51, the lumen portion 22 and the ball lens 52 are correctly determined without any adjustment.

It is recommended that in fixing the capillary tube 2, the capillary tube 2 be protected by coating a synthetic resin pipe 25.

In using the capillary tube 2, light from the light source is introduced into the capillary tube 2 via the ball lens 51 while a sample solution is caused to flow into the capillary tube 2. Efficient supply of light is performed without waste because the light is focused immediately before the bent portion for incident light 21 of the capillary tube 2 and slit 4 by use of the ball lens 51 and because radiant light parallel to the optical axis is given to the lumen portion 22 of the capillary tube 2.

Figure 2:
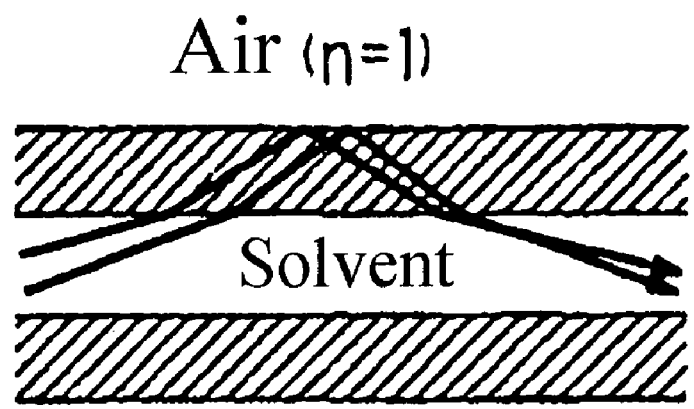
FIG. 2 is a diagram to explain the behavior of incident light in a lumen of the flow cell.

When light is introduced into the capillary tube 2, the light is transmitted through the interior of the capillary tube 2 because the refractive index of the liquid is larger than the refractive index of the air (n=1) around the capillary tube 2 (FIG. 2).

On that occasion, by increasing the inside diameter of the slit 4, it is possible to increase the quantity of light and to reduce noise.

The slit 4 is accurately positioned by forming the groove 76 of the cell body 71 and the groove 771 of the holding plate 77 as triangular grooves, whereby positioning was made unnecessary. On that occasion, however, there was a fear that a gap would occur between the slit 4 and the grooves 76 and 771. If in this case, light other than the light in the optical axis (stray light) comes in, this leads to a decrease in the sensitivity. For this reason, the ring 41 which cuts off stray light was adopted.

Figure 6:
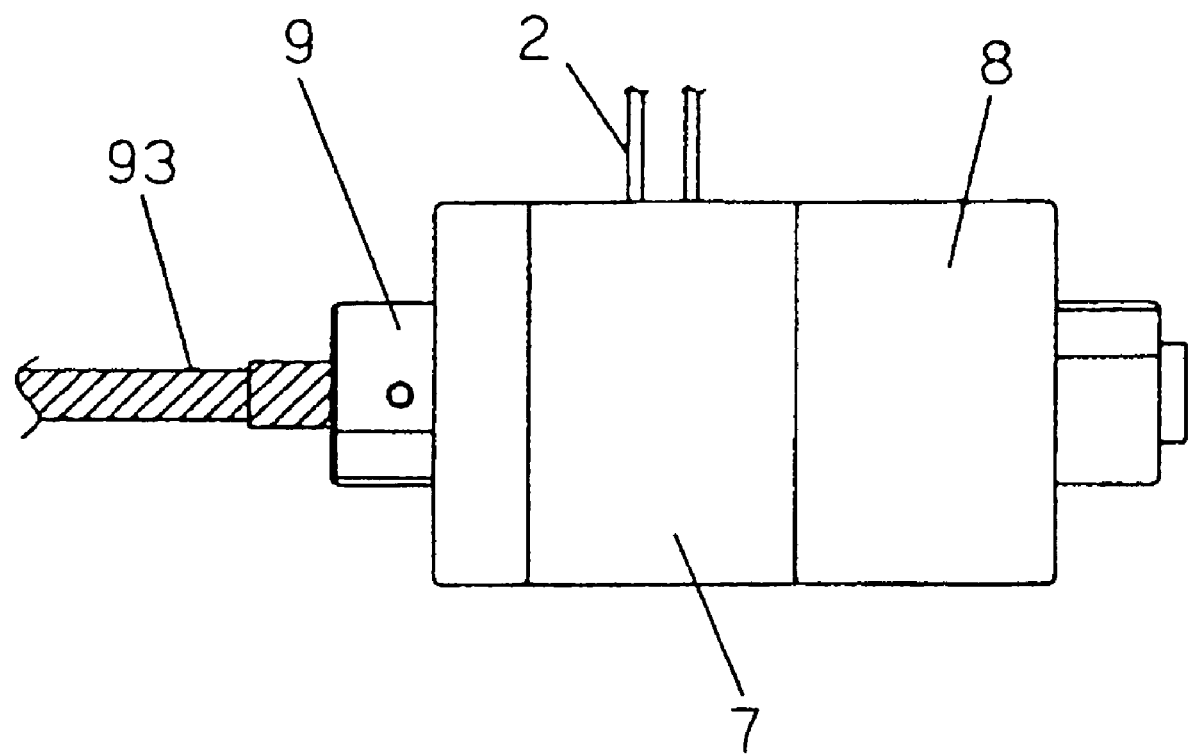
FIG. 6 is a partial explanatory view of a unit portion in an example of the present invention.
Figure 7:
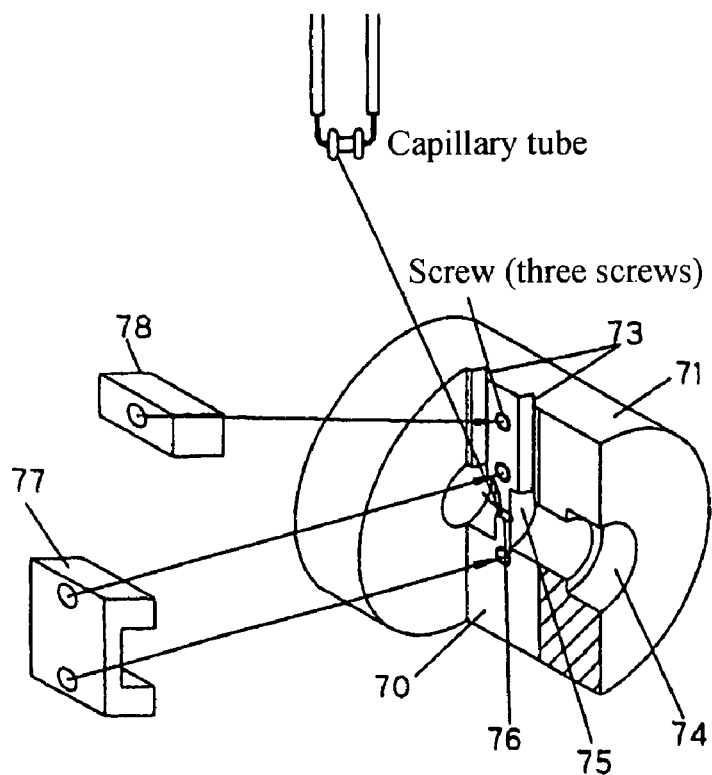
FIG. 7 is a partial exploded slant view of a capillary tube unit portion in an example of the present invention.
Figure 8:
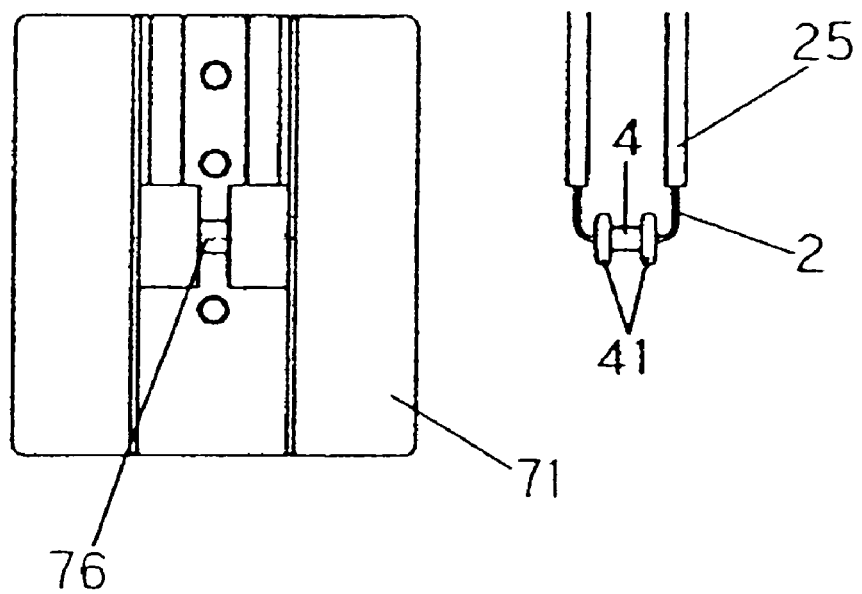
FIG. 8 is an exploded plan view of this portion.
Figure 12:
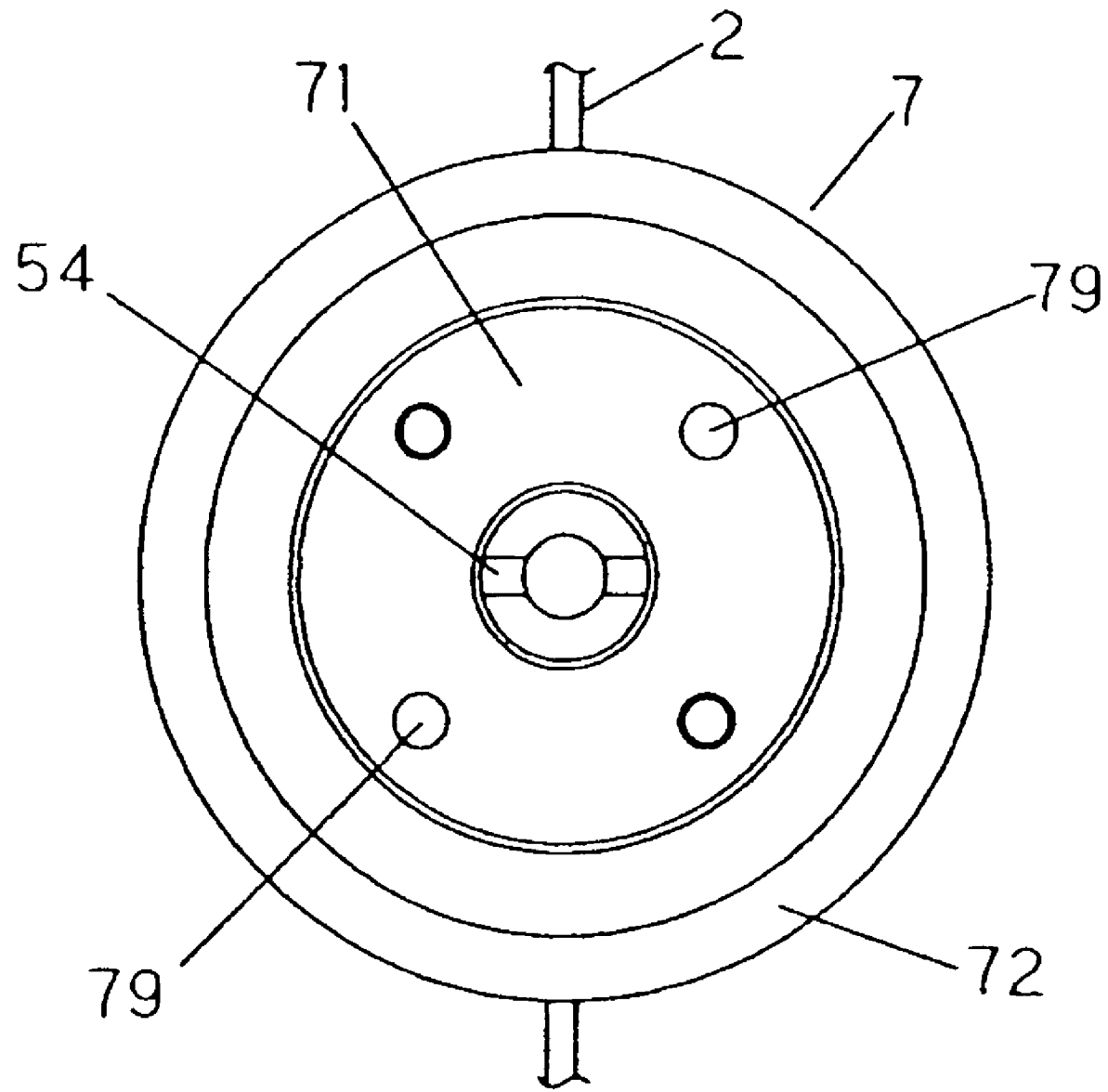
FIG. 12 is a front view of a capillary tube unit portion in an example of the present invention.
Figure 13A:
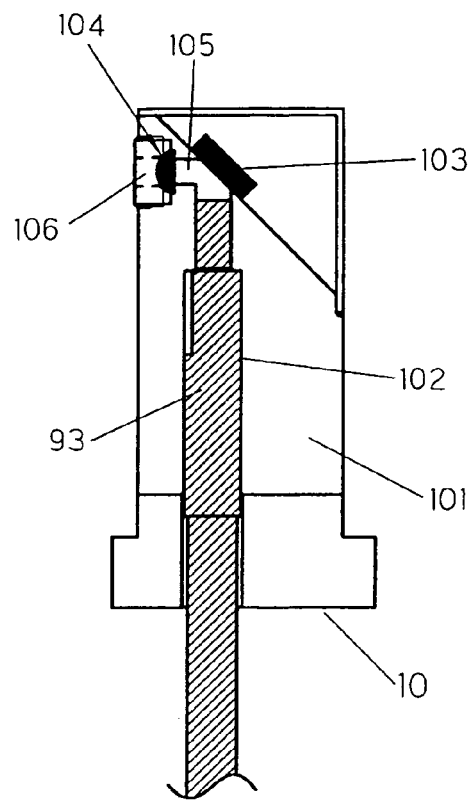
FIG. 13A is a partially enlarged longitudinal view to explain a light incident unit.
Figure 13B:
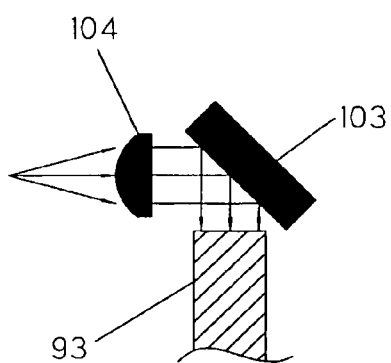
FIG. 13B is a partially enlarged longitudinal view to explain a light incident unit.

Although in FIGS. 6 and 10, the capillary tube unit 7, the sensor portion unit 8 and the light incidence unit 9 are connected together, they are each connectable by use of holes for pin 79, 79 as shown in FIG. 12.

In the sensor portion unit 8, a sensor 81 is set on a bed 83 and a function of transmission 82 to the detection section 6 is imparted according to each sample. In the light incidence unit 9, a through hole 92 is formed in a bed 91 and an optical fiber 93 is inserted into the through hole.

The leading end of this optical fiber 93 is in contact with the lens cover 54 end which holds the ball lens 51 of the capillary tube unit 7.

A light receiving section 10 to the optical fiber 93 is formed by inserting the optical fiber 93 end into a through hole 102 provided in a fiber holder 101 and fixing the optical fiber 93 end to the through hole 102. An optical passage 105 is formed at right angles to the through hole 102 end, a plan mirror 103 is installed at an angle of 45 degrees to this optical path 105 and the through hole 102, and a plane-convex lens 104 is installed on the optical path 105 by use of a lens holder 106, with the plane-convex lens 104 set in face-to-face relationship with the light source.

According to the above-described construction, by use of the optical fiber 93, it is possible to cause light to become incident on the lumen portion 23 of the capillary tube 2 via the ball lens 51. In general, when light is supplied from an optical fiber, incident light is weak and usually line noise is large. Therefore, it is difficult to use an optical fiber. In the present invention, the slit 4 is installed in the lumen portion 23 and the quantity of light is increased. Therefore, it is possible to reduce the line noise of a detector and hence an optical fiber can be used.

However, detection sensitivity decreases if the diameter of the slit 4 is too large. Therefore, it is necessary to select an appropriate slit. In the present invention, in the case of a capillary tube having an inside diameter of 0.075 mm and an outside diameter of 0.375 mm, a pipe having an inside diameter of 0.08 mm and an outside diameter of 1/16 Inch was used.

In the case of this slit 4, light departing from the optical axis can be positively cut by the ring 41, thereby contributing to a decrease in the line noise of the detector.

Figure 17:
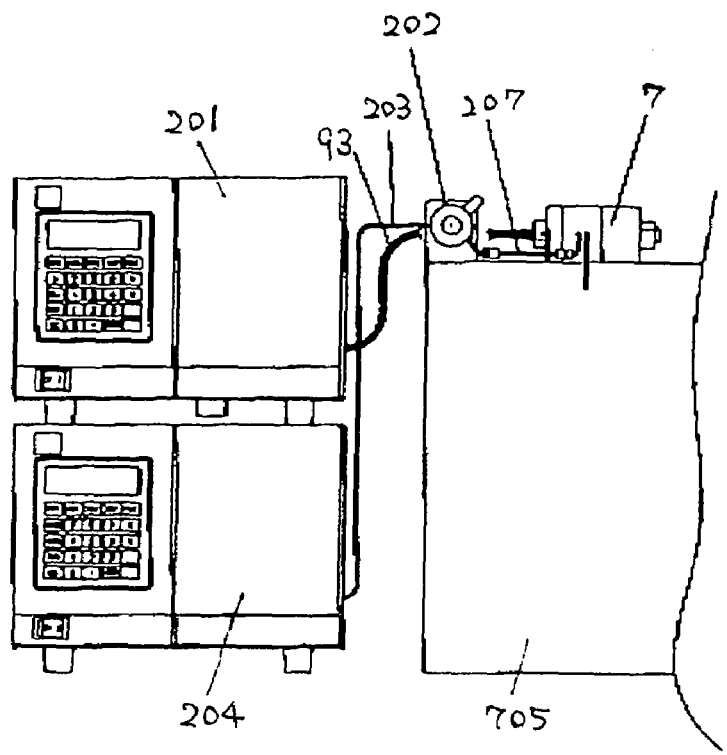
FIG. 17 is a schematic explanatory view of an example in which the present invention is connected to LC/MS.
Figure 18:
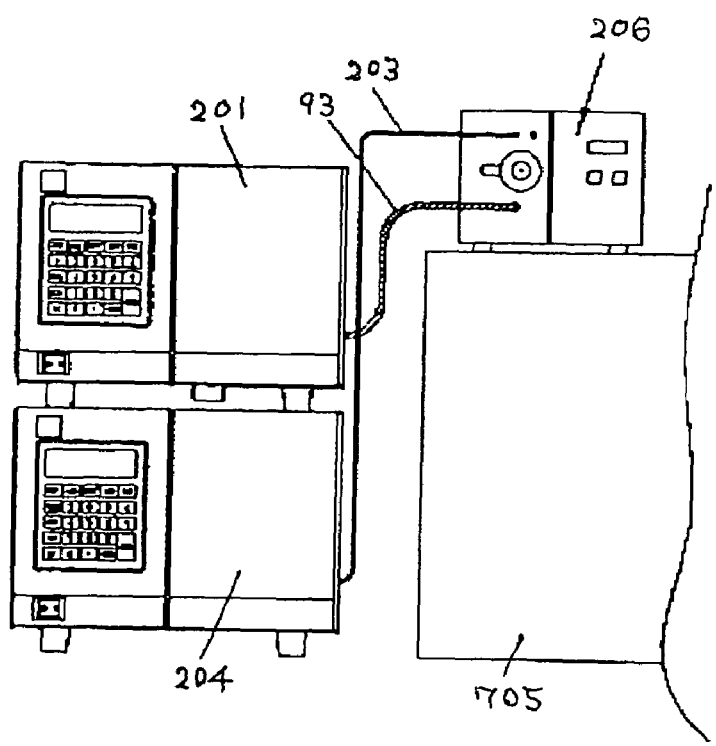
FIG. 18 is a schematic explanatory view of an example in which the present invention is connected to LC/MS and an oven is used.
Figure 19:
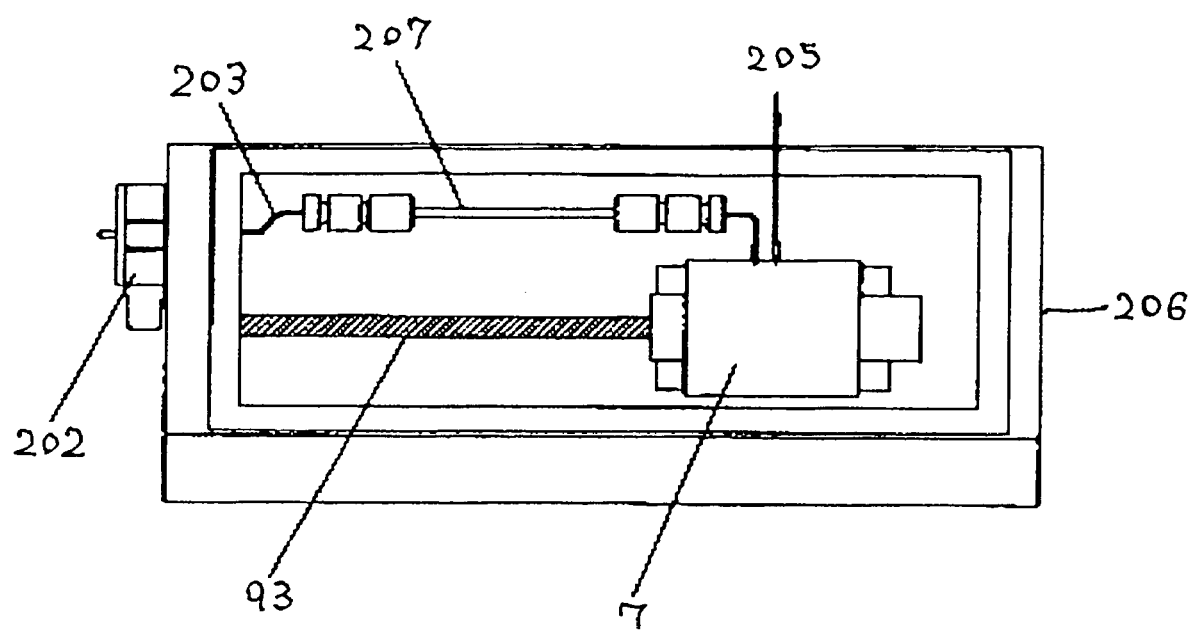
FIG. 19 is an explanatory view of a case where this oven is used.

FIGS. 17, 18 and 19 will be described.

In FIG. 17, the capillary tube unit 7 is connected to a light source of a UV detector 201 by the optical fiber 93 via the light incidence unit 9, and the capillary tube 2 is connected to a pump 204 via an injector 202 and a pipe 203. The capillary tube unit 7 is connected to LC/MS 205.

FIGS. 18 and 19 show an example in which the capillary tube unit 7, the light incidence unit 9 and the sensor portion unit 8 are housed in an oven 206. That is, the capillary tube unit 7, the light incidence unit 9 and the sensor portion unit 8 are built in the oven 206, and connected to a light source via the optical fiber 93 in the same manner as in FIG. 17, and the capillary tube 2 of the capillary tube unit 7 is connected to the pump 204 via a column 207, the pipe 203 and the injector 202.

The shortest connection is possible by making the column 207 and the LC/MS very close to the capillary tube unit 7. Each of the units and the column can be installed in the oven. However, it is not always necessary to install the flow cell in the oven because the capillary tube unit 7 is covered with a thermally insulated material.

Example 1

Figure 14:
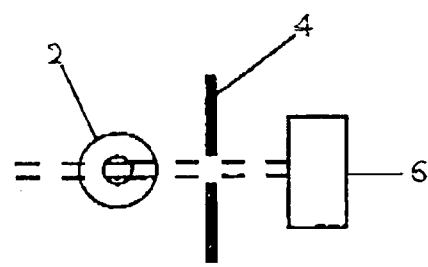
FIG. 14 is a schematic explanatory view of an optical system of a conventional cell portion.

As the present invention the structure shown in FIG. 1 was used and as a prior art the structure shown in FIG. 14 was used as an optical system which causes light to become incident in a direction orthogonal to the capillary tube flow passage. A comparative experiment of absorbance was conducted under the following conditions.

Conditions
    Wavelength: 254 nm
    Mobile phase: MeCN/$H_2O$=65:35
    Flow rate: 5 μl/min
    Standard sample for evaluation: Sample solution containing acetophenone, benzene, toluene and naphthalene in (MeCN/$H_2O$=65:35)
    Column: Inertsil® ODS-3 (0.3 mm i.d.×15 cm)
    Column temperature: Room temperature (23° C.)

Figure 15:
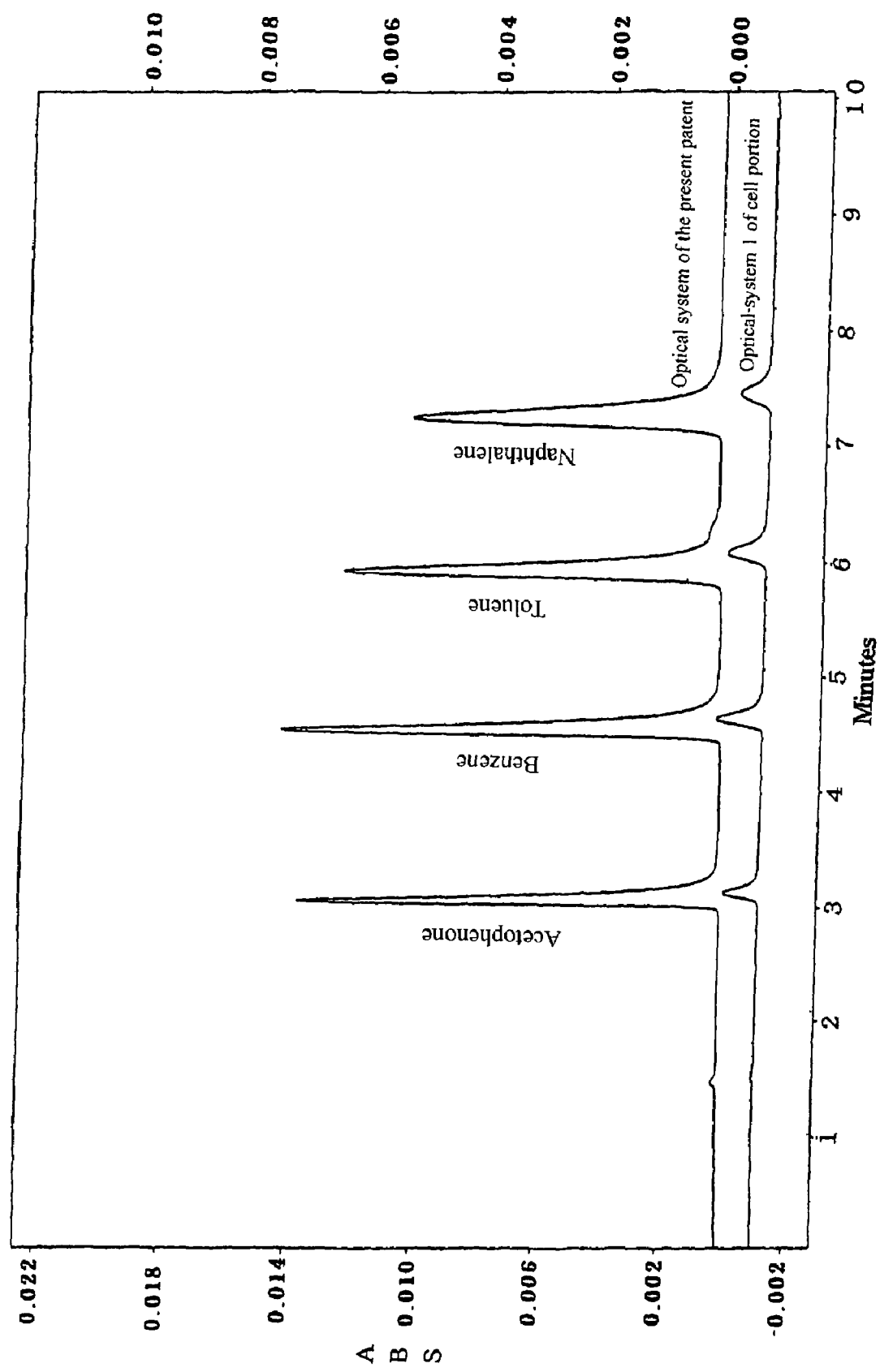
FIG. 15 is a chromatogram obtained in an experiment conducted using an optical system of the present invention and a conventional optical system.

As a result, the chromatogram shown in FIG. 15 was obtained.

The difference in absorbance is obvious, and the present invention exhibited higher sensitivity and peak height.

Example 2

The structure of the present invention shown in FIG. 1 was used and the structure shown in FIG. 1 from which the ring 41 was removed was used. A response experiment of an absorbance detector was conducted under the following conditions.

Conditions
    Response of detector: 0.1 sec and more
    Wavelength: 254 nm
    Mobile phase: MeCN/$H_2O$=65:35
    Flow rate: 5 μl/min
    Column temperature: Room temperature (23° C.)

Figure 16:
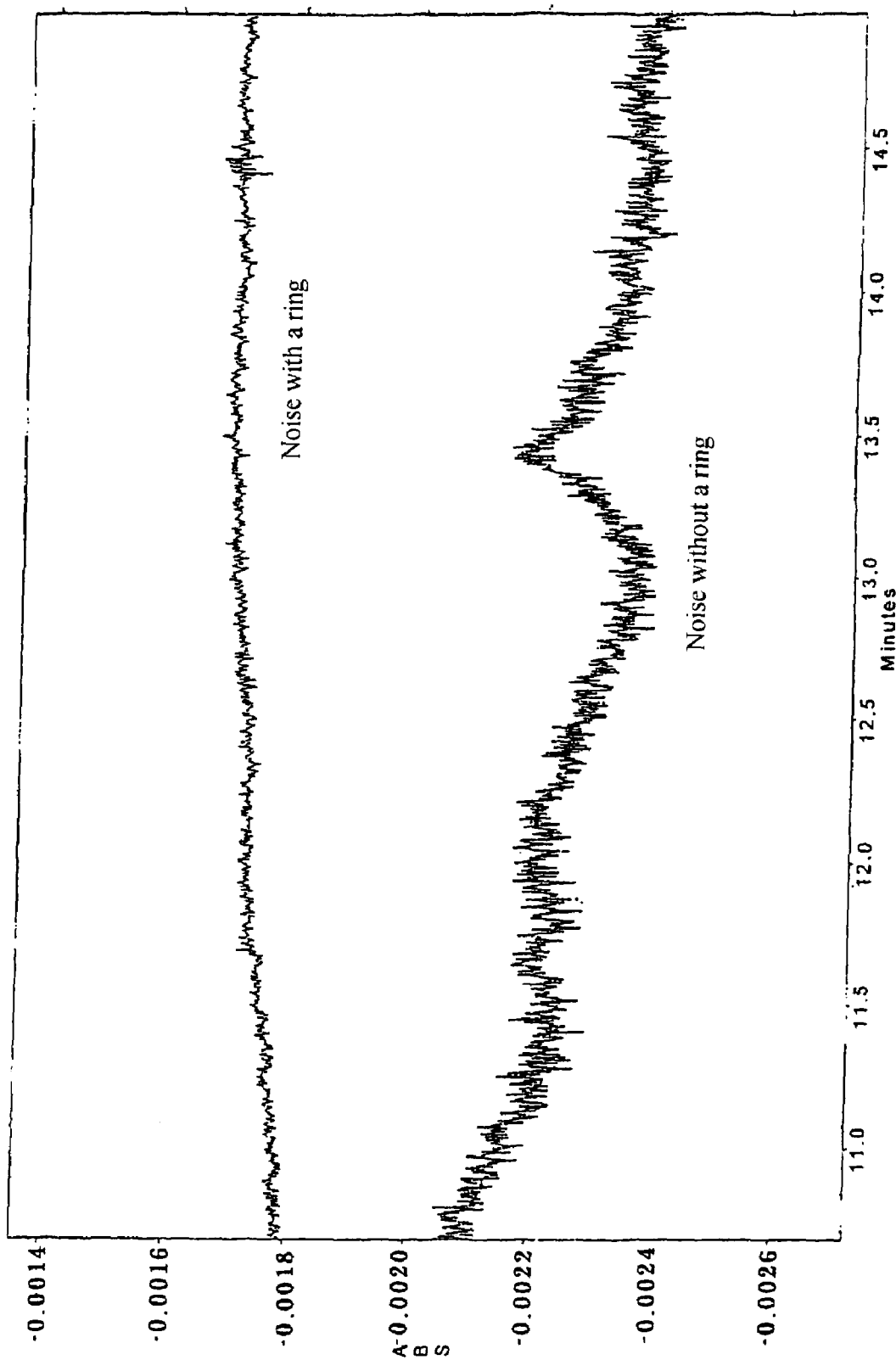
FIG. 16 is a chromatogram obtained in an experiment conducted using an optical system of the present invention and a conventional optical system with and without a ring.

As a result, the chromatogram shown in FIG. 16 was obtained.

The difference in the base line noise is obvious, and in the present invention the noise is kept in a low level and stability is good.

The capillary tube flow cell of the present invention is useful in analyses at very low flow rates. This capillary tube flow cell is particularly useful in a flow cell in which a capillary tube is used, because any user can perform replacement of capillary tubes easily and in a short time without requiring any adjustment when this replacement is necessary.

The invention claimed is:

1. A capillary tube flow cell in which a liquid sample is delivered and the liquid sample is exposed in a desired incident light for analysis purposes, the capillary tube flow cell comprising:
   a capillary tube which has a first bent portion for incident light and a second bent portion for emergent light, and a linear passage of a pre-determined length formed between the bent portions,
   a slit having a portion preventing stray light passage, wherein a portion of the linear passage of the capillary tube is inserted into the slit and wherein said portion preventing stray light passage is formed in a ring shape and fitted onto the slit or formed adjacent to the slit.

2. A capillary tube flow cell in which a liquid sample is delivered and the liquid sample is exposed in a desired incident light for analysis purposes, the capillary tube flow cell comprising:
   a capillary tube which has a first bent portion for incident light and a second bent portion for emergent light, and a linear passage of a pre-determined length formed between the bent portions,
   a slit having a portion preventing stray light passage, wherein a portion of the linear passage of the capillary tube is inserted into the slit and wherein the slit is formed as a pipe having an inner diameter through which the capillary tube passes; and
   a cell body having through holes formed on both side surfaces of the cell body,
   a lens holder which holds a ball lens placed insertable and fixable in the through hole,
   a wall formed between the through holes,
   a groove formed in the wall, and
   a tube holder,
   wherein the capillary tube and the pipe type slit are inserted through the groove, and the capillary tube is held by the tube holder.

3. A capillary tube flow cell in which a liquid sample is delivered and the liquid sample is exposed in a desired incident light for analysis purposes, the capillary tube flow cell comprising:
   a capillary tube which has a first bent portion for incident light and a second bent portion for emergent light, and a linear passage of a pre-determined length formed between the bent portions;
   a slit having a portion preventing stray light passage, wherein a portion of the linear passage of the capillary tube is inserted into the slit and wherein the slit is formed as a pipe having an inner diameter through which the capillary be passes;
   a cell body having through holes formed on both side surfaces of the cell body;
   a lens holder which holds a ball lens placed insertable and fixable in the through hole;
   a wall formed between the through holes;
   a groove formed in the wall; and
   a tube holder;
   wherein the capillary tube and the pipe type slit are inserted through the groove, and the capillary tube is held by the tube holder; and
   wherein the groove is a triangular groove.

4. A capillary tube flow cell in which a liquid sample is delivered and the liquid sample is exposed in a desired incident light for analysis purposes, the capillary tube flow cell comprising:
   a capillary tube which has a first bent portion for incident light and a second bent portion for emergent light, and a linear passage of a predetermined length formed between the bent portions;
   a slit encompassing at least a portion of the linear passage, the slit being formed as a pipe having an inner diameter through which the capillary tube passes, an inner diameter of the pipe being 0.05 to 1 mm larger than the outer diameter of the capillary tube;
   at least one ring portion formed with the slit or adjacent to the slit, the ring portion preventing stray light passage when the capillary tube flow cell is in use.

5. The capillary tube flow cell according to claim 4, further comprising:
   a cell body having through holes formed on both side surfaces of the cell body,
   a lens holder which holds a ball lens placed insertable and fixable in the through hole,
   a wall formed between the through holes,
   a groove formed in the wall, and
   a tube holder,
   wherein the capillary tube and the pipe type slit are inserted through the groove, and the capillary tube is held by the tube holder.

6. The capillary tube flow cell according to claim 5, wherein the groove is a triangular groove.

7. The capillary tube flow cell according to claim 5, wherein the cell body is covered with a thermally insulated synthetic resin cover.

8. The capillary tube flow cell according to claim 4, wherein a capillary tube unit is constituted by positioning a plurality of ball lenses in face-to-face relationship with the bent portion for incident light and the bent portion for emergent light each outside the bent portions, one of the ball lenses being removably provided with a light incidence unit having a light supply portion in communication with a light source and the other ball lens being removably provided with a sensor portion unit having a sensor.

9. The capillary tube flow cell according to claim 8, wherein the removable light incidence unit is connected to the light source and the capillary tube unit by use of an optical fiber and that the capillary tube unit is connected to a LC/MS.

* * * * *

UNITED STATES PATENT AND TRADEMARK OFFICE
CERTIFICATE OF CORRECTION

| | |
|---|---|
| PATENT NO. | : 7,667,837 B2 |
| APPLICATION NO. | : 10/556623 |
| DATED | : February 23, 2010 |
| INVENTOR(S) | : Iwano et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 578 days.

Signed and Sealed this

Seventh Day of December, 2010

David J. Kappos
*Director of the United States Patent and Trademark Office*